(12) United States Patent
Zimmerling

(10) Patent No.: US 9,907,963 B2
(45) Date of Patent: Mar. 6, 2018

(54) IMPACT PROTECTOR FOR AN EXTERNAL ELEMENT OF A PARTIALLY IMPLANTABLE SYSTEM

(75) Inventor: Martin Zimmerling, Patsch (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1199 days.

(21) Appl. No.: 12/277,812

(22) Filed: Nov. 25, 2008

(65) Prior Publication Data

US 2009/0143839 A1    Jun. 4, 2009

Related U.S. Application Data

(60) Provisional application No. 60/991,267, filed on Nov. 30, 2007.

(51) Int. Cl.
| | | |
|---|---|---|
| *A61N 1/36* | (2006.01) | |
| *A61N 1/375* | (2006.01) | |
| *H04R 25/00* | (2006.01) | |

(52) U.S. Cl.
CPC .......... *A61N 1/375* (2013.01); *A61N 1/36036* (2017.08); *H04R 25/606* (2013.01)

(58) Field of Classification Search
CPC .. A61N 1/375; A61N 1/0541; A61N 1/36032; A61N 1/36036
USPC ..................... 607/55–57, 136, 137
See application file for complete search history.

(56) References Cited

U.S. PATENT DOCUMENTS

| 3,520,503 | A | * | 7/1970 | McGehee | B64D 1/14 188/268 |
|---|---|---|---|---|---|
| 5,695,453 | A | * | 12/1997 | Neal | A61F 5/0118 602/21 |
| 5,948,006 | A | * | 9/1999 | Mann | A61N 1/08 128/903 |
| 6,389,318 | B1 | * | 5/2002 | Zarinetchi | H01F 38/14 607/60 |
| 7,974,700 | B1 | * | 7/2011 | Gibson | 607/55 |
| 8,150,502 | B2 | * | 4/2012 | Kumar | A61B 5/0006 600/509 |
| 8,660,658 | B2 | * | 2/2014 | Walsh | A61N 1/36032 381/312 |
| 2006/0003044 | A1 | * | 1/2006 | DiNello | B29C 41/18 425/412 |
| 2006/0058573 | A1 | | 3/2006 | Neisz et al. | 600/25 |
| 2007/0106344 | A1 | * | 5/2007 | Darley et al. | 607/55 |

(Continued)

FOREIGN PATENT DOCUMENTS

| WO | WO 2006/071210 | 7/2006 | ............... A61N 1/08 |
|---|---|---|---|
| WO | WO 2006/081361 | 8/2006 | ............... A61N 1/08 |

OTHER PUBLICATIONS

International Searching Authority, International Search Report and Written Opinion, dated Mar. 17, 2009, PCT/US2008/084665.

*Primary Examiner* — Michael D Abreu
(74) *Attorney, Agent, or Firm* — Sunstein Kann Murphy & Timbers LLP

(57) ABSTRACT

An external component housing is described for a cochlear implant system. A signal processing stage is contained within the housing for generating an electrical signal for an implanted portion of the system. An external coil is also within the housing for transmitting the electrical signal transcutaneously through the skin of a patient to the implanted portion. An impact absorber shields the system components from the impact energy associated with a mechanical impact to the housing.

7 Claims, 2 Drawing Sheets

(56) References Cited

U.S. PATENT DOCUMENTS

2008/0009919 A1* 1/2008 Zierhofer .................. 607/57
2009/0034769 A1* 2/2009 Darley et al. ............. 381/328

* cited by examiner

IMPACT PROTECTOR FOR AN EXTERNAL ELEMENT OF A PARTIALLY IMPLANTABLE SYSTEM

This application claims priority from U.S. Provisional Patent Application 60/991,267, filed Nov. 30, 2007, which is incorporated herein by reference.

FIELD OF THE INVENTION

The present invention generally relates to cochlear implant systems, and specifically to the external structures of such systems.

BACKGROUND ART

Cochlear implants (CI) help profoundly deaf or severely hearing impaired persons to perceive environmental sounds. Unlike conventional hearing aids, which just apply an amplified and modified sound signal, a cochlear implant is based on direct electrical stimulation of the auditory nerve. The intention of a cochlear implant is to stimulate nervous structures in the inner ear electrically in such a way that hearing impressions most similar to normal hearing are obtained.

A cochlear implant system essentially consists of two parts, an external speech processor and the implanted stimulator. The speech processor contains a power supply and is used to perform signal processing of the acoustic signal to extract stimulation parameters for the implanted stimulator. The implanted stimulator generates stimulation patterns and conducts them to auditory nervous tissue by an electrode array which usually is positioned in the scala tympani in the inner ear. Inductive coupling across the skin is used to transfer both the required electrical power and the processed audio information to the implanted components. An external transmitter coil (coupled to the external signal processor) is placed on the skin adjacent to a subcutaneous receiver coil (connected to an implanted receiver). Often, a magnet in the external coil structure interacts with a corresponding magnet in the subcutaneous secondary coil structure. This arrangement inductively couples a radio frequency (rf) electrical signal to the receiver, which is able to extract from the rf signal both the audio information for the implanted portion of the system and a power component to power the implanted system.

Some recipients of cochlear implants (CI's) also have problems with their vestibular system, which increases the risk that they will loose their balance and fall. When that happens, the side of their head containing the implant may receive a mechanical impact, which among other things, may result in damage to the implant.

Thus, the implant needs to be designed to withstand mechanical impacts. But making an implant very robust may have the disadvantage that it becomes too physically large (especially with children). Furthermore, if the implant is extremely strong, there is additional risk that a fall related mechanical impact may cause a bone fracture of the implant bed. One alternative possibility is to place the implant anatomically at a location which is less prone to a mechanical impact. But that solution is not possible for every implant and stimulator type, for example, because the implanted electrode wires might be too long, etc.

SUMMARY OF THE INVENTION

Embodiments of the present invention are directed to an impact resistant external component housing for a cochlear implant system. A signal processing stage is contained within the housing for generating an electrical signal for an implanted portion of the system. An external coil is also within the housing for transmitting the electrical signal transcutaneously through the skin of a patient to the implanted portion. An impact absorber shields the system components from the impact energy associated with a mechanical impact to the housing. For example, the system components shielded by the impact protector may include the implanted portion of the system.

In one specific embodiment, the impact absorber may include a housing reinforcement element for distributing the impact energy towards an outer perimeter of the housing. For example, the reinforcement element may be a housing cover over a portion or all of the outer surface of the housing. In addition or alternatively, impact absorber may include a damping element within the housing for cushioning the housing components from the impact energy.

In another specific embodiment, there may also be a positioning magnet for cooperating with a corresponding internal magnet of the implanted portion to hold the housing on the skin in proper position for operation of the system, in which the impact absorber shields the positioning magnet from the impact energy.

The impact absorber may include a bottom surface of the housing which is placed against the skin. For example, the bottom surface may include rounded edges around an outer perimeter of the housing and/or may include cushioning material over the bottom surface for absorbing the impact energy. In a specific embodiment, the impact protector may distribute the impact energy to the external coil so as to increase the coil diameter and transfer the impact energy away from the implanted portion. The external component housing may be made of one of the materials typically used for such applications, for example, a ceramic material.

DETAILED DESCRIPTION OF SPECIFIC EMBODIMENTS

Figure 1:
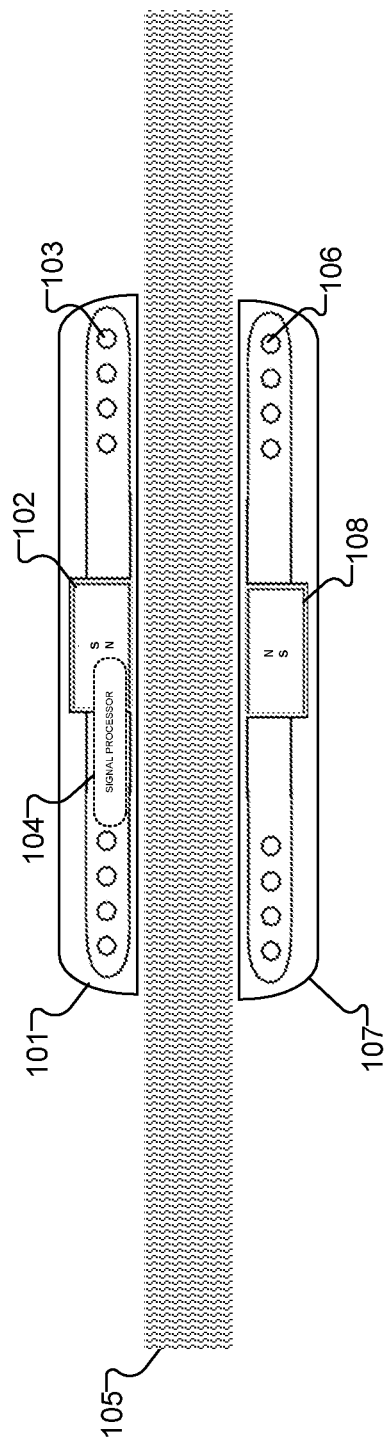
FIG. 1 shows an example of the coil arrangement of a partially implantable system as known in the prior art.

Various embodiments of the present invention are directed to an impact resistant external component housing for a cochlear implant system. FIG. 1 shows an example of the coil arrangement of a cochlear implant system as known in the prior art. An external coil housing 101 contains various external components associated with the implant system including an external coil 103 for transmitting an electrical implant signal through the patient's skin 105 to a corresponding implant coil 106 contained within an implant housing 107. The external coil housing 101 may also contain a signal processing stage 104 which generates the electrical implant signal. Typically, the implant signal includes both a power component for providing electrical power to the implanted components of the system, and also a data component representing information for use in the implanted components of the system. For example, in the specific case of a cochlear implant system, the data component typically is a digitized version of an audio signal representing the near acoustic environment as sensed by a microphone within the signal processing stage 104. Other specific systems may have signal processing elements in a physically separate module so that the external coil housing 101 simply receives the electrical implant signal and transmits it through the external coil 103 across the patient's skin 105 to the implant coil 106.

The external coil housing 101 also contains an external holding magnet 102 centered within the housing and the external coil 103. The external coil housing 101 is placed on the patient's skin 105 at the site of the implant housing 107 which also has its own corresponding internal holding magnet 108. The magnetic attraction across the patient's skin 105 between the internal holding magnet 102 and the external holding magnet 108 securely maintains the external coil 103 in a proper operational position with respect to the internal coil 106. This arrangement allows the electrical implant signal to be transmitted across the patient's skin 105 from the external coil 103 to the internal coil 106 for use by the implanted portion of the system.

Figure 2:
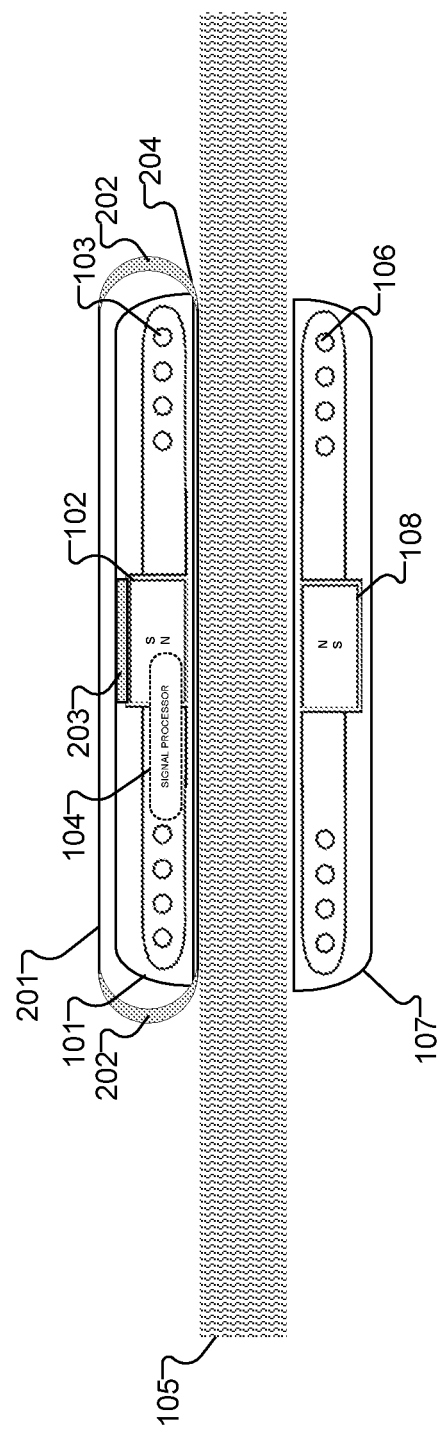
FIG. 2 shows an improved coil arrangement according to one embodiment of the present invention.

FIG. 2 shows an improved external component housing according to one embodiment of the present invention, including impact absorbing elements which can shield other components, both external and implanted, from some of the impact energy resulting from mechanical impact to the housing. Such arrangements may also shield the surrounding skin and bone of patient from the adverse effects of an impact. As shown in FIG. 2, the external coil housing 101 is covered by a housing cover 201 which shields the underlying elements from the impact energy of a mechanical impact. When struck, the housing cover 201 evenly distributes the impact energy over the entire area of the housing cover 201, and away from the underlying components, both the immediately vulnerable external components in the external coil housing 101 and also the underlying implanted components within the implant housing 107. In addition, the incision site in the patient's skin 105 and the underlying bone also is shielded from the impact energy which the housing cover 201 directs radially outward. In some specific embodiments, the housing cover 201 may be strengthened by reinforcing ribs 202 which may also help with directing the impact energy radially outward. In addition, the bottom rim 204 of the housing cover 201 has a smooth rounded edge shaped to divert the impact energy to the more robust parts of the housing cover 201 such as the outer perimeter of the reinforcing ribs 202. The smooth rounded edge of the bottom rim 204 protects the underlying skin flap of the implant incision and reduces the risk of a sharper edge embedding in the patient's skin 105 in the event of a mechanical impact. The bottom rim 204 may be formed of a relatively soft material to provide further impact protection.

Also within external coil housing 101 is a cushion pad 203 under the top center of the housing cover 201 that absorbs the impact energy from any mechanical impacts. For example, cushion pad 203 may be a pad of soft resilient material which prevents a mechanical impact from directly affecting the components within the external coil housing 101, but instead directs the impact energy outward towards the outer perimeter and across the entire area of the housing cover 201.

In addition, the external coil 103 itself can be designed so that in the case of an impact, the top part of the external coil 103 increases its diameter, thus distributing the impact energy over a greater surface area and diverting some of the impact energy to areas away from the implanted portions of the system.

Such impact protection elements in the external portion of the implant system reduce the possibility that a mechanical impact will damages or creates defects in the system, especially the relatively hard to access implanted portions of the system. The impact protections features also reduce the probability and severity of head injuries around the implant. The impact protection features are also generally available for retro-fitting on previous implant systems which do not have the same desired robustness to mechanical impact. Embodiments may also be especially useful for systems using an implant with a relatively brittle ceramic housing which may be especially susceptible to adverse effects from any mechanical impacts. Limitations of such designs are affected by the weight of the external coil 103, the structural materials (preferably non-metallic) and the available space within and near to the external coil housing 101.

Although various exemplary embodiments of the invention have been disclosed, it should be apparent to those skilled in the art that various changes and modifications can be made which will achieve some of the advantages of the invention without departing from the true scope of the invention.

What is claimed is:

1. An external component arrangement for a cochlear implant system for a patient, the cochlear implant system further including an implanted portion having implanted components including an implant coil, the external component arrangement comprising:
    an external housing, the entire external housing configured for placement external to the skin of the patient, the external housing containing:
        i. a signal processing stage enclosed within the external housing, the signal processing stage for generating an electrical signal for the implanted portion of the system, and
        ii. an external coil enclosed within the external housing, the external coil for transmitting the electrical signal transcutaneously through the skin of the patient to the implant coil of the implanted portion; and
    an impact absorber containing the external housing wherein the impact absorber shields system components within the external housing and underlying implanted components from a mechanical impact to the impact absorber which produces an associated impact energy, wherein the impact absorber includes reinforcing ribs which distribute the impact energy towards an outer perimeter of the external component arrangement.

2. An external component arrangement according to claim 1, wherein the impact absorber includes a bottom surface of the external component arrangement which is placed against the skin.

3. An external component arrangement according to claim 2, wherein the bottom surface includes rounded edges around an outer perimeter of the external component arrangement.

4. An external component arrangement according to claim 2, further comprising:
    cushioning material over the bottom surface for absorbing the impact energy.

5. An external component arrangement according to claim 1, further including a cushioning element within the external housing for cushioning system components within the external housing from the impact energy.

6. An external component arrangement according to claim 1, further comprising:
    a positioning magnet for cooperating with a corresponding internal magnet of the implanted portion to hold the external housing on the skin in proper position for operation of the system, wherein the impact absorber shields the positioning magnet from the impact energy.

7. An external component arrangement according to claim 1, wherein the external housing is made of a ceramic material.

* * * * *